United States Patent [19]

Bergeron

[11] Patent Number: 5,623,950
[45] Date of Patent: Apr. 29, 1997

[54] SECURITY COVER

[75] Inventor: Claude Bergeron, Chicoutini, Canada

[73] Assignee: Genimedic Inc., Jonquiere, Canada

[21] Appl. No.: 437,873

[22] Filed: May 9, 1995

[30] Foreign Application Priority Data

May 10, 1994 [CA] Canada ................................. 2123291

[51] Int. Cl.⁶ ................................................. A61B 19/00
[52] U.S. Cl. ............................ 128/869; 128/872; 5/494
[58] Field of Search ................................. 128/845, 846, 128/869, 872, 873, 874, 875, 876; 5/482, 494

[56] References Cited

U.S. PATENT DOCUMENTS

| 568,986 | 10/1896 | Nagel | 128/872 |
|---|---|---|---|
| 1,590,522 | 6/1926 | Kalman | 128/872 |
| 4,653,131 | 3/1987 | Diehl | 128/872 |
| 4,742,821 | 5/1988 | Wootan | 128/873 |
| 5,044,025 | 9/1991 | Hunsinger et al. | |

*Primary Examiner*—Michael A. Brown
*Attorney, Agent, or Firm*—Merek & Voorhees

[57] ABSTRACT

A security cover for preventing a person lying on a bed from falling off the bed having a cover made of a flexible but sturdy material and a line removably fastened to the longitudinal sides of the bed. The cover includes loops mounted on each sides. The loops may be secured to the line in sliding relationship so that the cover forms, with the mattress, an enclosed space around the person lying on the bed thereby preventing this person from falling off the bed.

10 Claims, 6 Drawing Sheets

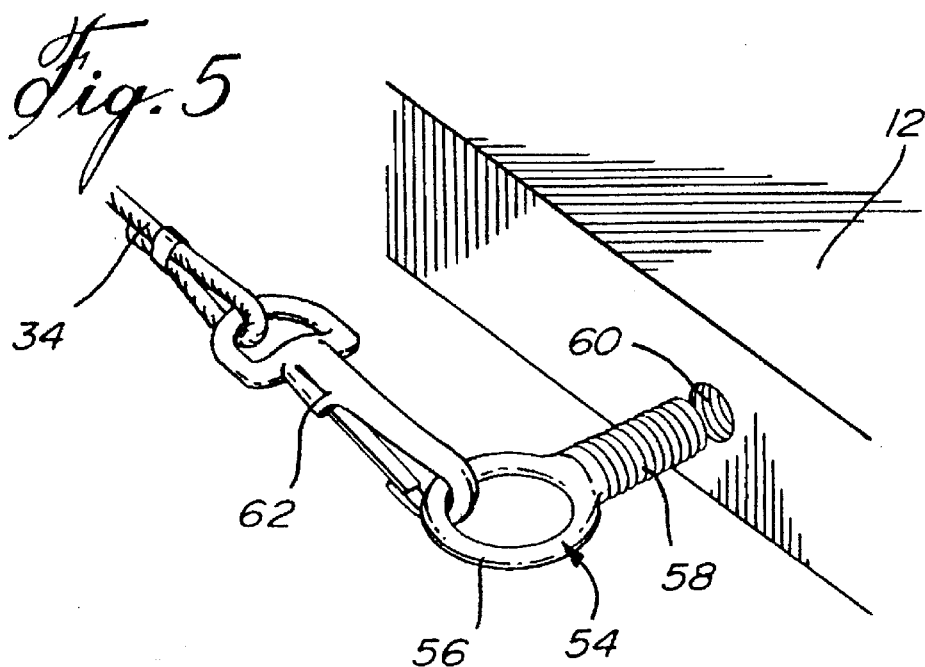
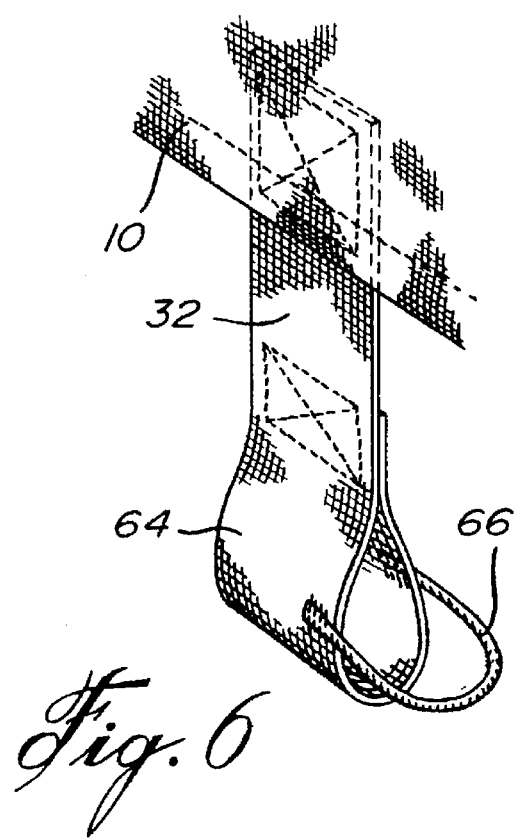

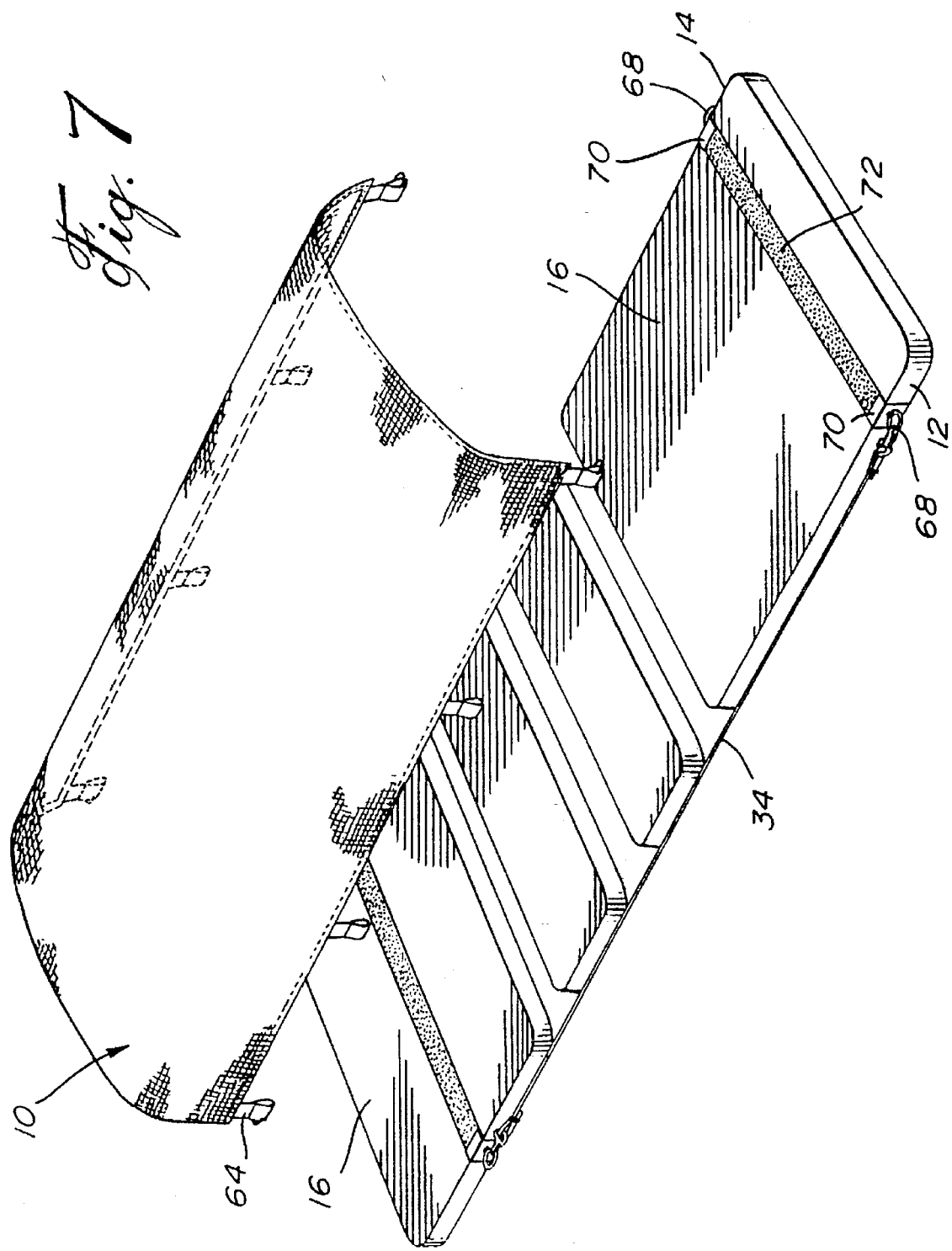

SECURITY COVER

FIELD OF THE INVENTION

The present invention relates to security devices adaptable to hospital beds or other beds. More particularly, the present invention relates to an apparatus for preventing a person lying on a bed from falling off the bed.

BRIEF DESCRIPTION OF THE PRIOR ART

In hospitals, nursing homes and the like, it is widely known that it may become necessary, for various reasons, to use an apparatus for preventing a person lying on a bed from falling off the bed during periods when the patient is unsupervised.

For example, if a patient is agitated in his sleep, he may fall off the bed, perhaps inflicting serious injuries upon himself. In hospitals, it is common for hospital workers to pull up rails mounted on the sides of hospital beds to prevent patients from rolling off the bed. In most cases where the patient is not overly agitated, the use of such side rails is generally satisfactory. However, if the patient becomes quite agitated or confused, the patient may easily climb over the side rails and subsequently injure himself.

Similar circumstances occur when hospital bed side rails will be insufficient to protect patients who become aggressive, very agitated, delirious, or who purposely attempts to climb over the side rails and off the bed. Again, it is possible for the patient to seriously injure himself by falling off the bed or side rails. In many cases, the hospital staff have resorted to restraining patients by attaching their wrists and ankles to the side rails using specially designed restraint straps. While this procedure will generally prevent the patient from falling off the bed, it also has many disadvantage. Firstly, it is not visually pleasing, for example for visiting loved ones, to see a patient physically restrained to a bed. Secondly, the patient may become uncomfortable and will be unable to change his position on the bed, resulting in perhaps long periods of discomfort and perhaps bruising of the patient. Thirdly, the restraint straps used to attach the wrists and ankles of the patient are generally difficult to clean. Finally, the extent of time and effort necessary for hospital staff to install and remove the physical restraints is also a disadvantage.

There is therefore clearly a need for an improved apparatus for preventing a person lying on a bed from falling off the bed.

OBJECTS OF THE INVENTION

An object of the present invention is therefore to provide an improved apparatus for preventing a person lying on a bed from falling off the bed. The novel apparatus being free from the above discussed limitations and drawbacks identified in the prior art.

SUMMARY OF THE INVENTION

More specifically, in accordance with the present invention, there is provided a security cover apparatus for use in preventing a person lying on a bed from falling off said bed, said bed being the type having a mattress mounted on a mattress support, said mattress support including two opposite longitudinal sides, said apparatus comprising:

a security cover having opposite longitudinal sides;

cooperating securing means on said cover and said mattress support, wherein said cover may be releasably mounted to said mattress support to thereby form, with said mattress, an enclosed space around said person lying on said bed thereby preventing said person from falling off said bed.

In accordance with a preferred embodiment of the present invention, there is provided a security cover apparatus for use in preventing a person lying on a bed from falling off said bed, said bed being the type having a mattress mounted on a mattress support, said mattress support including two opposite longitudinal sides, said apparatus comprising:

a cover having opposite longitudinal sides;

cooperating securing means on said cover and said mattress support, said securing means on said mattress support include a line extended along each said longitudinal sides of said mattress support, each said lines having opposite ends each provided with hooks, each said lines being removably mounted between two rigid posts provided on each said longitudinal sides of said mattress support, each said posts including a ring shaped head cooperating with said hooks for removable engagement of said hooks on said rigid posts, each said rigid posts being mounted on an individual bracket, said brackets being secured to said longitudinal sides of said mattress support two-by-two by means of a band of elastically deformable material joining two brackets and extended between said longitudinal sides of said mattress support; said securing means on said cover include a plurality of loop elements disposed along said longitudinal sides of said cover, said loop elements being adapted to be traversed by said line;

fastening means provided on said longitudinal sides of said cover, said fastening means including loop elements being adapted to cooperate with said hooks of said line, wherein said cover may be releasably fastened to said hooks at a predetermined position with respect to said mattress support; wherein said cover may be releasably mounted to said mattress support to thereby form, with said mattress, an enclosed space around said person lying on said bed thereby preventing said person from falling off said bed.

In another aspect, the present invention is concerned with a kit of parts for forming a security cover apparatus for use in preventing a person lying on a bed from falling off said bed, said bed being the type having a mattress mounted on a mattress support, said mattress support including two opposite longitudinal sides, said kit of parts comprising the following parts:

a security cover having opposite longitudinal sides;

cooperating securing means on said cover and said mattress support, wherein said cover may be releasably mounted to said mattress support to thereby form, with said mattress, an enclosed space around said person lying on said bed thereby preventing said person from falling off said bed.

Other objects, advantages and other features of the present invention will become more apparent upon reading of the following non restrictive description of preferred embodiments thereof, given by way of example only with reference to the accompanying drawings.

BRIEF DESCRIPTION OF THE DRAWINGS

In the appended drawings:

FIG. 5 illustrates a post and a line according to a second embodiment of the present invention;

FIG. 6 illustrates a hook according to the second embodiment of the present invention;

FIG. 7 illustrates a third embodiment of the apparatus preventing a person from falling from a bed according to the present invention;

DETAILED DESCRIPTION OF THE PREFERRED EMBODIMENTS

Figure 1:
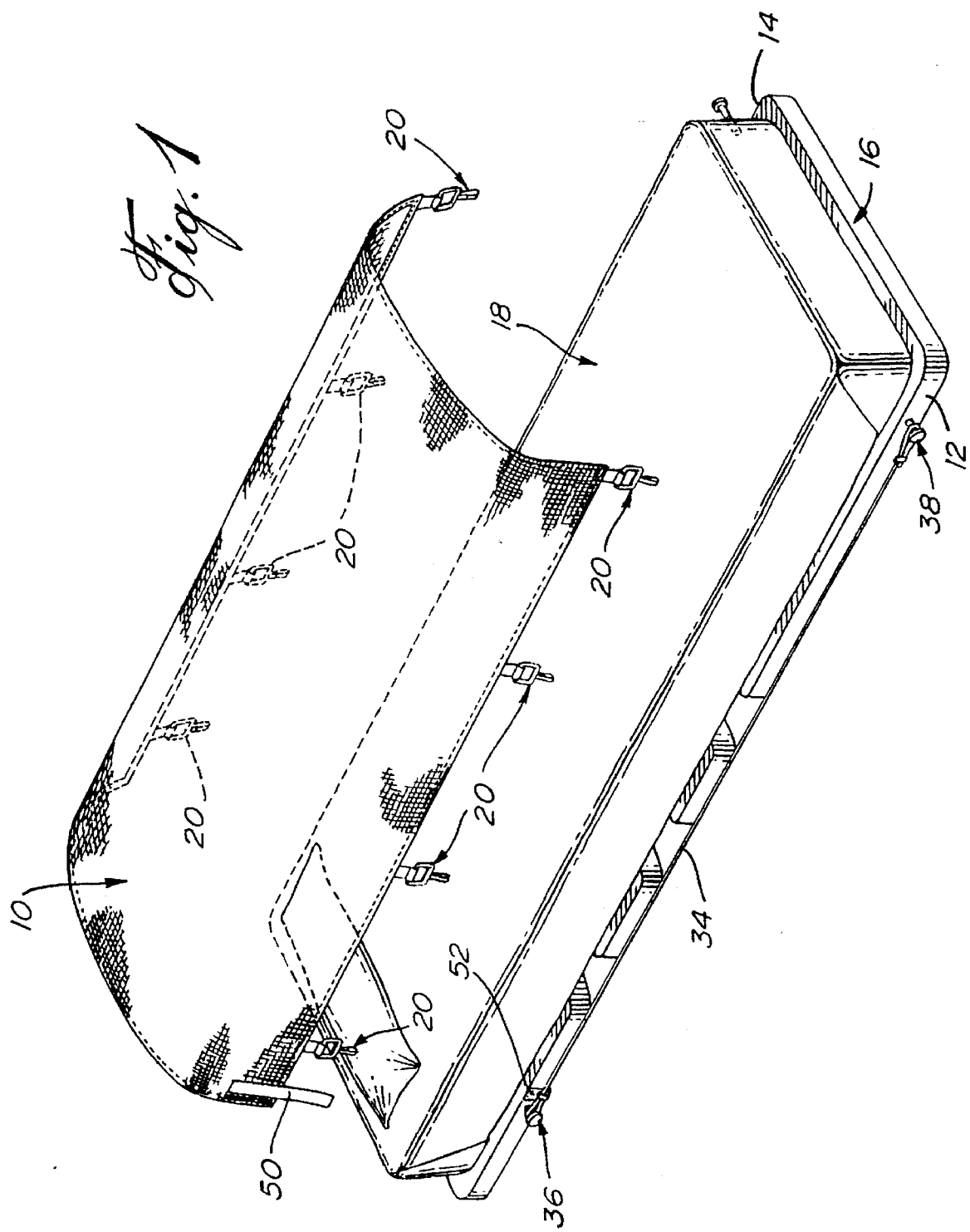
FIG. 1 illustrates a perspective view of a first embodiment of the apparatus for preventing a person from falling from a bed according to the present invention.

Referring now to FIGS. 1 to 4, a first embodiment of an apparatus for preventing a person from falling from a bed according to the present invention will be described.

The apparatus comprises a cover 10 which can be removably secured to the sides 12 and 14 of a mattress support 16. The mattress support 16 is conventionally used to support a mattress 18. The cover 10 includes a plurality of snap hooks 20 mounted to the sides of the cover 10.

The cover 10 is advantageously made of a flexible and sturdy material such as canvas, tarpaulin, or the like.

Figure 4:
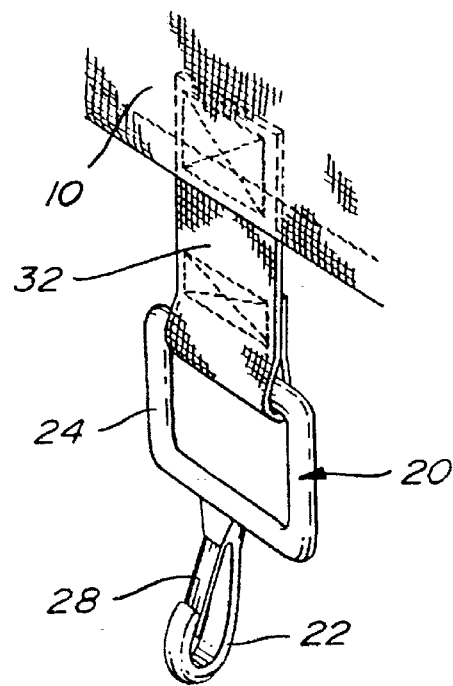
FIG. 4 illustrates a hook according to the first embodiment of the present invention.

Referring to FIG. 4, the snap hooks 20 comprise a conventional snap hook portion 22 and a fastening ring 24. The fastening ring 24 is fixedly mounted to the cover 10 through a flexible link 32 advantageously made of a material comparable to the material forming the cover 10.

Figure 3:
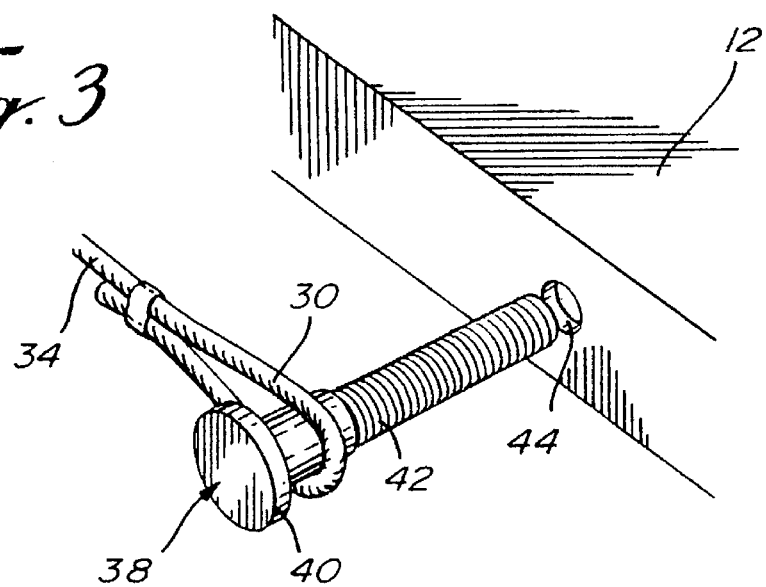
FIG. 3 illustrates a post and a line according to the first embodiment of the present invention.

Returning to FIG. 1, the apparatus also includes a line 34 on each sides 12, 14 of the mattress support 16 (only one shown). The line 34 is mounted to the side 12 through two posts 36 and 38, fixedly mounted to the mattress support 16. FIG. 3 illustrates post 38 which includes a circularly shaped head 40 and an externally threaded shank 42. The side 12 of the mattress support 16 comprises an aperture 44 sized to allow the introduction of the shank 42. A nut (not shown) is used to fasten the post 38 in place when it is fully inserted in the aperture 44. As illustrated, the line 34 forms a loop 30 at its end to thereby allow the line 34 to be traversed by the shank 42 prior to the insertion of the shank 42 into aperture 44, thereby attaching the line 34 to the side 12 through the post 38.

The line 34 is therefore fixedly mounted to the side 12 of the mattress support 16. As illustrated in FIG. 1, the length of the line 34 is such that when it is extended between the two posts 36 and 38, it is moderately tight.

Figure 2:
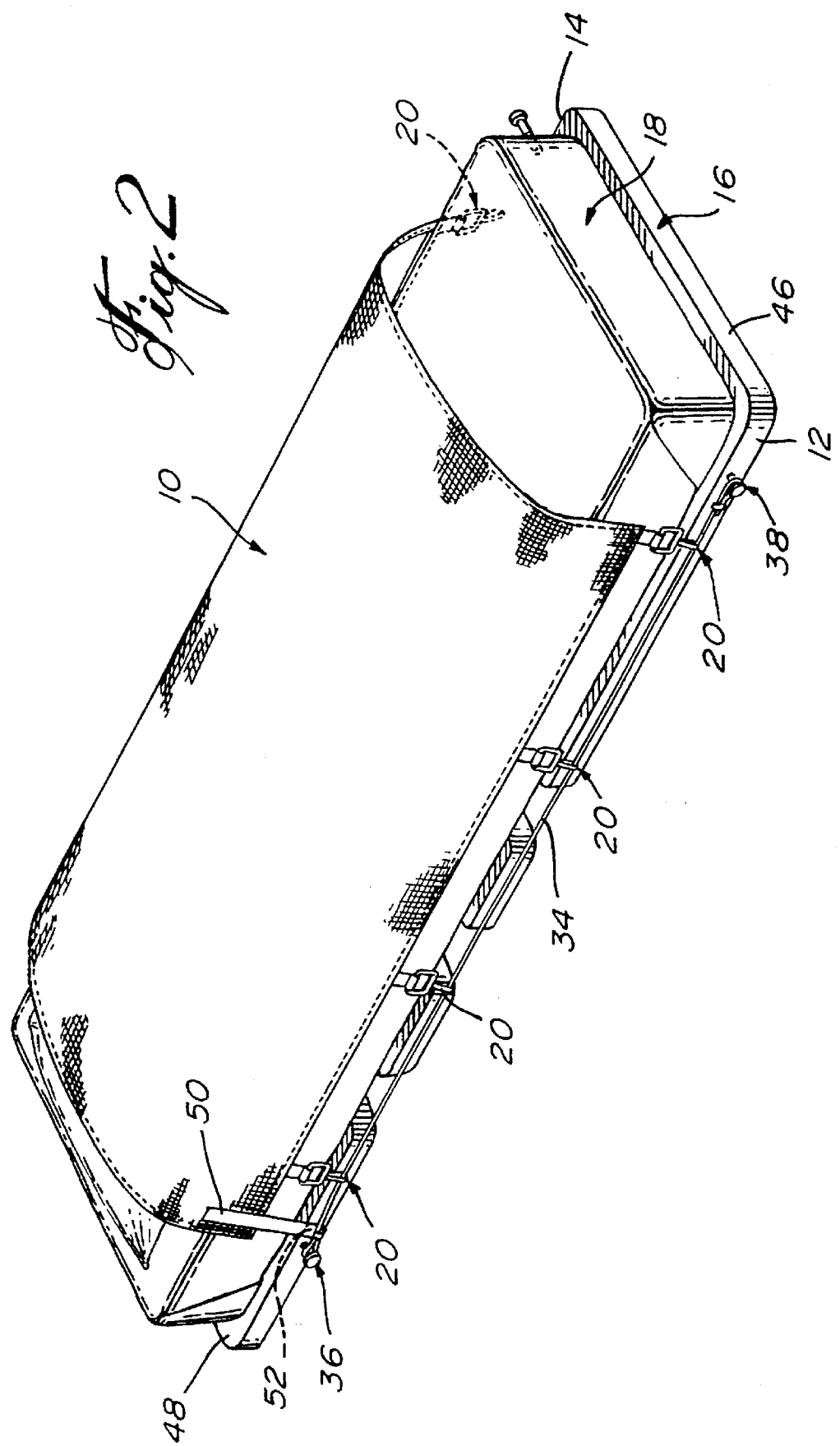
FIG. 2 illustrates a perspective view of the embodiment of FIG. 1 with the cover installed in its operating position.

As illustrated in FIG. 2, the snap hooks 20 may be secured to the line 34. More specifically, the line 34 may be introduced in the snap hooks 20 through the unbiasing of a spring 28 closing the opening of the snap hook 20.

It is to be noted that the line 34 has a diameter such that it allows the snap hooks 20 to longitudinally slide onto the line 34 after they are traversed by the line 34.

The cover 10 and the sides of the mattress support 16 also comprise cooperating loops and hooks type fasteners, the function of which will be explained hereinafter. A male part 50 is mounted to the cover 10 while a female part 52 is mounted to the side 12 of the mattress support 16.

In operation, when a person needs to be maintained in a bed so that there are no risks that the person falls off, the cover 10 is placed over the person and the snap hooks 20 are engaged to the line 34. The last step is to engage the fastener 50 to the fastener 52 so as to prevent the sliding of the cover 10 onto the line 34.

Another way of performing the operation is to engage the snap hooks 20 to the line 34 beforehand, slide the cover 10 toward the foot end 46 of the mattress support 16, place the person on the bed and then slide the cover 10 toward a head end 48 of the mattress support 16. Again, the last step is to engage the fastener 50 to the fastener 52 so as to prevent the sliding of the cover 10 toward the foot end 46 onto the line 34.

A second embodiment of the present invention will now be described with references to FIGS. 5 and 6 which illustrate the differences between the second embodiment and the first embodiment.

FIG. 5 illustrates a post 54 having a ring-shaped head 56 mounted on an externally threaded shank 58. The side 12 of the mattress support 16 includes an internally threaded aperture 60 corresponding to the threaded shank 58. Therefore, the post 54 may be manually screwed into the aperture 60 of the side 12.

Also illustrated in FIG. 5 is an end of the line 34 to which is mounted a conventional snap hook 62. The snap hook 62 may releasably be connected to the ring-shaped head of the post 54. Therefore, since a second post similar to post 54 is mounted to the side 12 of the mattress support 16 (see FIGS. 1 and 2), the line 34 may be releasably extended substantially parallel to the side 12 of the mattress support 16. Of course, the side 14 of the mattress support 16 is also provided with a line, similar to line 34, releasably extended between two posts, similar to post 54.

FIG. 6 illustrates a loop 64 which replaces the snap hook 20 illustrated in FIG. 4. Of course, many loops 64 are provided on each sides of the cover 10.

The loop 64 is advantageously made of a material similar to the material forming the cover 10. Therefore, the cover 10 may be easily washed since it is entirely made of fabric material.

Since the line 34 may be removed from the posts 54, the installation of the cover 10 to the line 34 may be done by detaching one end of the line 34 from its post 54, slipping the loops 64 on the line 34, and to attach the snap hook 62 to the post 54.

Also illustrated in FIG. 6 is a second fastening loop 66 replacing the cooperating loops and hooks type fasteners 50, 52 illustrated in FIGS. 1 and 2. Indeed, the fastening loop 66 may be inserted in the snap hook 62, thereby preventing the sliding of the cover 10 onto the line 34.

Figure 8:
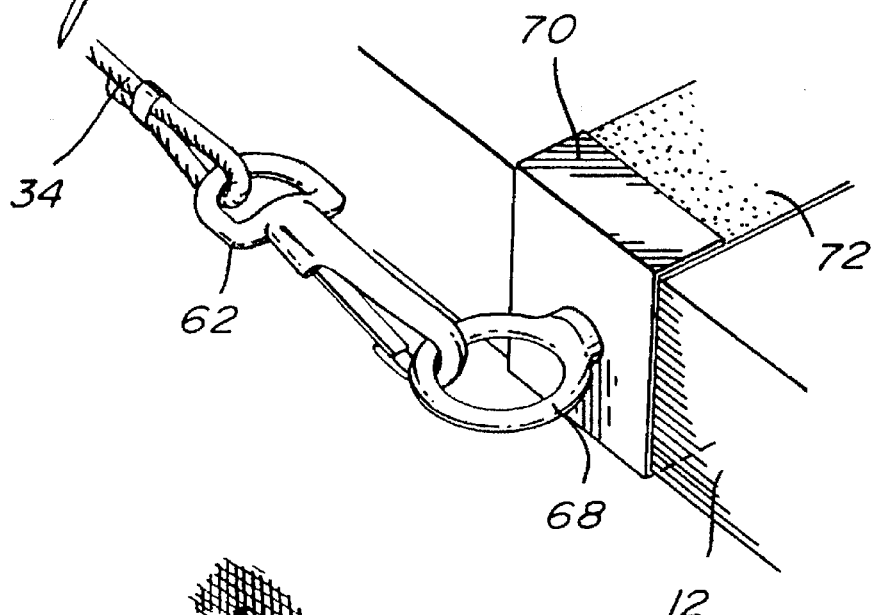
FIG. 8 illustrates a post according to the third embodiment of the present invention.
Figure 9:
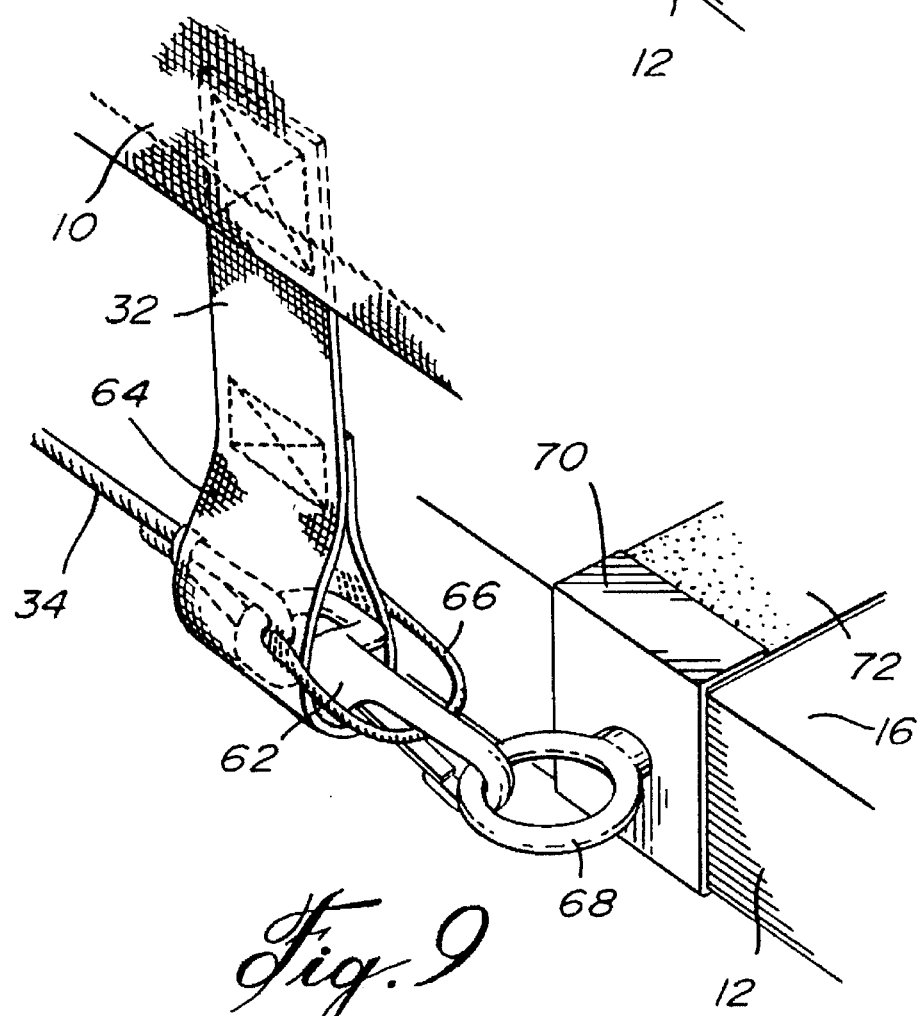
FIG. 9 illustrates a loop according to the third embodiment of the present invention.

Referring now to FIGS. 7 to 9, a third embodiment of the present invention will be described. The third embodiment is very similar to the second embodiment. The major difference is that in the third embodiment, it is not necessary to make modifications to the mattress support 16. Indeed, to install the posts 38 and 54 of the first and second embodiments, respectively, it is necessary to provide the sides 12 and 14 of the mattress support 16 with apertures necessary to attach the posts 38 or 54.

As illustrated in FIG. 8, a ring-shaped post 68 is fixedly mounted to a U-shaped bracket 70. The bracket 70 is dimensioned to be mountable to the side 12 of the mattress support 16. A band of elastically deformable material 72 is used to connect two brackets 70 together (see FIG. 7). The length of the band 72 is somewhat smaller than the width of the mattress support 16. Therefore, it is necessary to elastically deform the band 72 to install it to the mattress support 16. This deformation of the band 72 ensure an essentially stable position of the brackets 70 with respect to the mattress support 16.

FIG. 9 illustrates a loop 64 slidably secured to the line 34, and a fastening loop 66 fastened to the snap hook 62. Therefore, the cover 10 is maintained in a predetermined position with respect to the mattress support 16 since the cover 10 cannot slide onto line 34.

Although the present invention has been described hereinabove by way of preferred embodiments thereof, these embodiments can be modified at will, within the scope of the appended claims, without departing from the spirit and nature of the subject invention.

What is claimed is:

1. A security cover apparatus for use in preventing a person lying on a bed from falling off said bed, said bed being of the type having a mattress mounted on a mattress support including two opposite longitudinal sides, said security cover apparatus comprising:

a pair of apertured hooking elements mounted to each said longitudinal sides of said mattress support;

a pair of flexible lines each having respective first and second ends provided with hooks; each said flexible line being removably extendable along one longitudinal side of said mattress support between said apertured hooking elements and secured in place by the passage of each said hook in one of said apertured hooking elements;

a security cover having opposite longitudinal sides and made of a sturdy material; said security cover including a plurality of securing loop elements mounted to each said longitudinal sides thereof; said securing loop elements being adapted to be slidably traversed by said flexible line; said security cover further including fastening loop elements mounted to said longitudinal sides thereof; said fastening loop elements being removably mountable to one of said (i) hook of said flexible line and (ii) said hooking elements whereby:

(a) said securing loop elements allow said cover to be releasably mounted to said mattress support to thereby form, with said mattress, an enclosed space around said person lying on said bed thereby preventing said person from falling off said bed; and (b) said fastening loop elements prevent unintentional sliding of said securing loop elements on said flexible lines.

2. A security cover apparatus as defined in claim 1, wherein said securing loop elements of said security cover are loops made of a sturdy material and stitched to said longitudinal sides of said security cover.

3. A security cover apparatus as defined in claim 1, wherein said cover includes small apertures to allow a portion of the body heat to exit.

4. A security cover apparatus as defined in claim 1, wherein said hooks provided at each said ends of each said flexible lines are snap hooks.

5. A security cover apparatus as defined in claim 1, wherein each said apertured hooking element of one of said two longitudinal sides is linked to an apertured hooking element of the other of said two longitudinal sides by a band of material.

6. A security cover apparatus as defined in claim 5, wherein said bands of material are removably mountable to said two longitudinal sides of said mattress support.

7. A security cover apparatus as defined in claim 6, wherein said bands of material are made of elastically deformable material.

8. A security cover apparatus as defined in claim 7, wherein each said apertured hooking element is mounted to an individual bracket, said band of elastically deformable material joining two brackets mounted to opposite longitudinal sides of said mattress support and extends between said longitudinal sides of said mattress support.

9. A security cover apparatus for use in preventing a person lying on a bed from falling off said bed, said bed being the type having a mattress mounted on a mattress support including two opposite longitudinal sides, said security cover apparatus comprising:

a pair of rigid posts mounted to each said longitudinal sides of said mattress support; each said rigid post being mounted on an individual bracket; said brackets being secured to said mattress support two-by-two by means of a band of elastically deformable material; each said post including a ring-shaped head;

a pair of flexible lines each having respective first and second ends provided with hooks adapted to cooperate with the ring-shaped heads of said rigid posts; each said flexible line being removably extendable along on side of said mattress support between said rigid posts and secured in place by the passage of each said hook in one of said ring-shaped head of said rigid posts;

a security cover having opposite longitudinal sides and made of a sturdy material; said security cover including a plurality of securing loop elements disposed along said longitudinal sides of said cover, said loop elements being adapted to be slidably traversed by said flexible line; said security cover further including fastening loop elements mounted to said longitudinal sides thereof; said fastening loop elements being removably mountable to said hooks of said flexible line;

whereby (a) said securing loop elements allow said cover to be releasably mounted to said mattress support to thereby form, with said mattress, an enclosed space around said person lying on said bed thereby preventing said person from falling off said bed, and (b) said fastening loop elements prevent unintentional sliding of said securing loop elements on said flexible lines.

10. A kit of parts for forming a security cover apparatus for use in preventing a person lying on a bed from falling off said bed, said bed being the type having a mattress mounted on a mattress support including two opposite longitudinal sides, said kit of parts comprising the following parts:

a pair of rigid posts mounted to each said longitudinal sides of said mattress support; each said rigid post being mounted on an individual bracket; said brackets being secured to said mattress support two-by-two by means of a band of elastically deformable material; each said post including a ring-shaped head;

a pair of flexible lines each having respective first and second ends provided with hooks adapted to cooperate with the ring-shaped heads of said rigid posts; each said flexible line being removably extendable along on side of said mattress support between said rigid posts and secured in place by the passage of each said hook in one of said ring-shaped head of said rigid posts;

a security cover having opposite longitudinal sides and made of a sturdy material; said security cover including a plurality of securing loop elements disposed along said longitudinal sides of said cover, said loop elements being adapted to be slidably traversed by said flexible line; said security cover further including fastening loop elements mounted to said longitudinal sides thereof; said fastening loop elements being removably mountable to said hooks of said flexible line;

whereby (a) said securing loop elements allow said security cover to be releasably mounted to said mattress support to thereby form, with said mattress, an enclosed space around said person lying on said bed thereby preventing said person from falling off said bed, and (b) said fastening loop elements prevent unintentional sliding of said securing loop elements on said flexible lines.

* * * * *